United States Patent [19]

Cummings

[11] Patent Number: 5,208,164

[45] Date of Patent: May 4, 1993

[54] PROCESS FOR MONITORING ALKANOLAMINE SOLUTIONS

[75] Inventor: Arthur L. Cummings, Ponca City, Okla.

[73] Assignee: Conoco Inc., Ponca City, Okla.

[21] Appl. No.: 695,498

[22] Filed: May 2, 1991

[51] Int. Cl.$^5$ ............................................. G01N 27/04
[52] U.S. Cl. .................................... 436/79; 208/207; 208/236; 208/237; 422/82.02; 423/228; 423/229; 436/73; 436/109; 436/120; 436/129; 436/146; 436/150
[58] Field of Search ................ 436/73, 79, 150, 109, 436/120, 129, 146; 422/82.02; 564/497, 503; 208/207, 236, 237; 423/228, 229

[56] References Cited

U.S. PATENT DOCUMENTS

| | | |
|---|---|---|
| 2,628,191 | 2/1953 | Sard . |
| 2,797,188 | 6/1957 | Taylor, Jr. et al. ................ 564/497 |
| 3,246,759 | 4/1966 | Matalon . |
| 3,531,252 | 9/1970 | Rivers . |
| 4,199,323 | 4/1980 | Miller et al. . |
| 4,242,097 | 12/1980 | Rich et al. . |
| 4,814,281 | 3/1989 | Byers . |
| 4,880,513 | 11/1989 | Davis et al. . |

*Primary Examiner*—Robert J. Warden
*Assistant Examiner*—Timothy M. McMahon

[57] ABSTRACT

(a) An alkanolamine solution containing anions, a conductance probe connected through a meter to a recorder and a stirrer are provided in a container, (b) the solution is stirred at a constant rate and metering and recording of the conductance of the alkanolamine solution are initiated, (c) an anion exchange resin in the OH$^-$ form is then introduced to the container in an amount in excess of that required to exchange all anions from the amine solution, (d) the conductance of the alkanolamine solution is monitored until steady state is reached, and (e) the total anion content and the sodium content (if present) are determined from the conductance trace.

The process and apparatus may be used to display conductance changes with time and rate of conductance changes with time in order to determine which anions are present in the alkanolamine solution, whether or not sodium is present and the magnitude of conductance values at various time intervals.

22 Claims, 7 Drawing Sheets

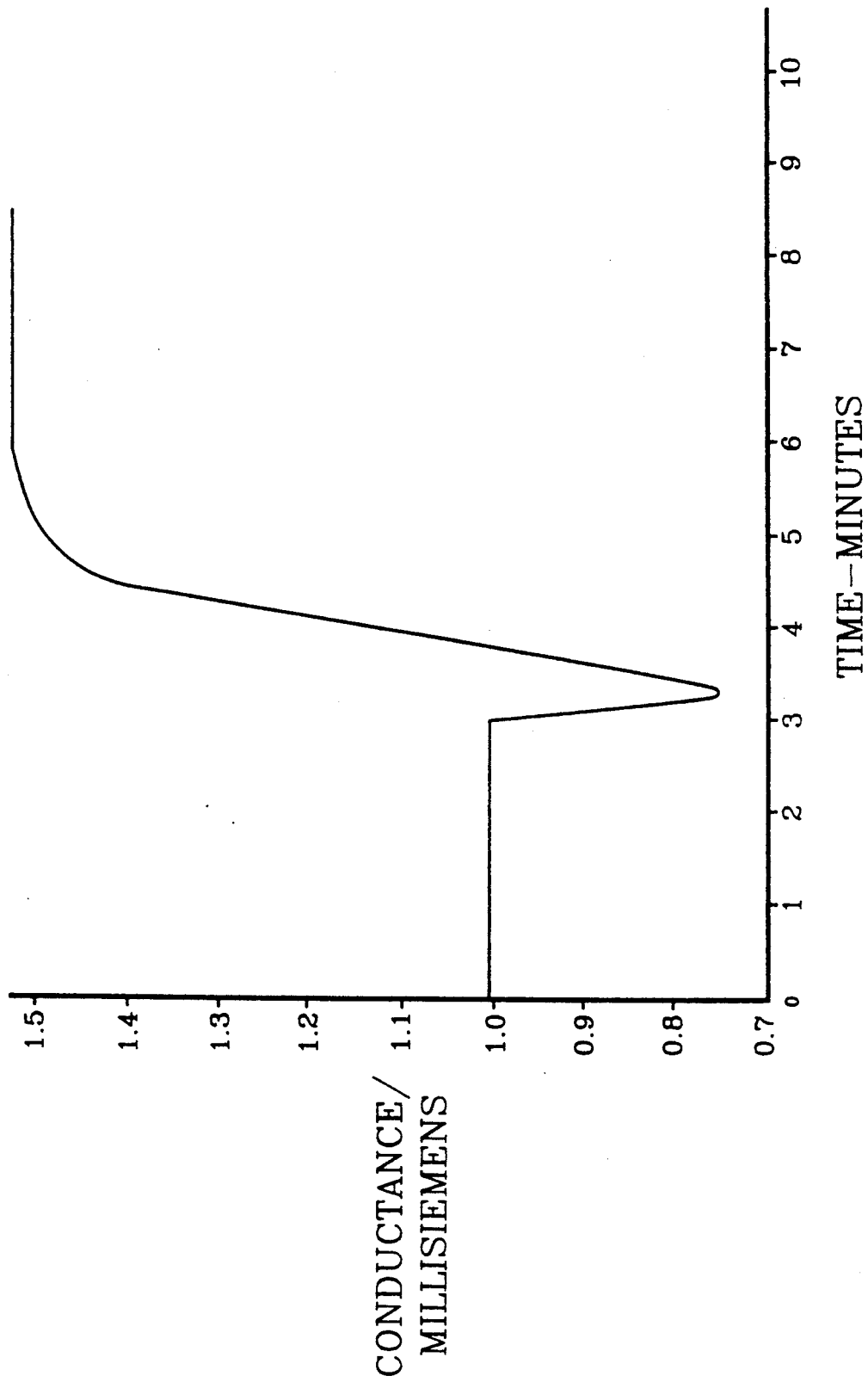

PROCESS FOR MONITORING ALKANOLAMINE SOLUTIONS

BACKGROUND OF THE INVENTION

Alkanolamine sweetening units are used for the removal of $H_2S$ and $CO_2$ from natural gases, enhanced oil recovery gases, refinery hydrodesulfurizer recycle gases, FCCU and Coker gas plant tail gases, LPG streams, and Claus sulfur recovery tail gases. The alkanolamines (AAmines) commonly used are ethanolamine, diethanolamine, methyl diethanolamine, diisopropanol amine, and triethanol amine. These compounds are weak bases in aqueous solution. When solutions of alkanolamines are contacted in packed, sieve plate, bubble cap, or valve tray columns with streams containing $H_2S$ and $CO_2$, the $H_2S$ and $CO_2$ dissolve into the alkanolamine solution. The following chemical reactions then take place:

$$H_2S + AAmine = AAmine\ H^+ + HS^-$$

$$H_2O + CO_2 + AAmine = AAmineH^+ + HCO_3^-$$

General Eqn.: Acid Gases + Alkanolamine = Alkanolamine Salts of Acid Gases

The solution of water, unreacted alkanolamine, and alkanolamine salts is subjected to steam stripping to reverse the above reaction and remove $H_2S$ and $CO_2$ from the alkanolamine. The $H_2S$ and $CO_2$ removed from the alkanolamine can then be processed by Claus sulfur recovery, incineration, fertilizer manufacture, or other means.

$H_2S$ and $CO_2$ are not the only gases in the above referred to streams which form weak acids when dissolved in water. Other such acid gases, as they are commonly called, that may appear in gas streams treated with alkanolamine include $SO_2$, COS, or HCN. These gases also undergo the same reactions as $H_2S$ and $CO_2$ to form alkanolamine salts. These salts, however, cannot be removed by steam stripping as are $H_2S$ and $CO_2$ salts. Thus, they remain and accumulate in the system.

Another problem is presented if oxygen gets into the alkanolamine system. Oxidation of acid gas conjugate base anions leads to the formation of other alkanolamine salts, most commonly salts of thiosulfate $S_2O_3^=$ and sulfate $SO_4^=$. Alkanolamine salts are also formed with thiocyanate ($SCN^-$) and chloride ($Cl^-$ These salts also cannot be regenerated by steam stripping.

Alkanolamine salts which cannot be heat regenerated, called heat-stable salts, reduce the effectiveness of alkanolamine treating. The alkanolamine is protonated and cannot react with $H_2S$ and $CO_2$, which dissolve into the solution. Also, accumulated alkanolamine salts are known to cause corrosion in carbon steel equipment which is normally used in amine systems. These salts are also known to cause foaming problems which further decreases treating capacity.

One procedure used to deprotonate the alkanolamine, so it can react with $H_2S$ and $CO_2$, is to add an alkali metal hydroxide, such as NaOH, to the amine solution. The deprotonated alkanolamine then can then be returned to $H_2S$ and $CO_2$ removal service. However, the sodium salts of the anions of the heat-stable salts are also heat stable, are difficult to remove, and thus accumulate in the alkanolamine solution with attendant corrosion and foaming problems.

The alkanolamine solution containing alkali metal salts of anions which form heat-stable salts with such alkanolamine may be regenerated by contacting it with a cation exchange resin whereby alkali metal ions are removed from the solution and thereafter contacting the solution with a basic anion exchange resin to remove the heat stable anions from the solution. The anion exchange resin is thereafter regenerated with a dilute sodium hydroxide, and the cation exchange resin is regenerated with a dilute mineral acid. The two resins are flushed with water before and after the regeneration procedures.

In another procedure, described in U.S. Pat. No. 2,797,188, alkanolamine solution containing heat-stable salts of the alkanolamines with thiocyanates and formates is regenerated in a two-stage process. In the first stage, the solution is contacted with a strong base anion exchange resin which has a high affinity for the thiocyanate anions. The solution leaving the first stage, which is substantially reduced and/or free of thiocyanate anions is then contacted in the second stage with the same type of ion exchange resin wherein formate anions are substantially removed. The process is continued until breakthrough of thiocyanate anions from the first stage resin when the process is halted. Regeneration of the first stage resin is carried out by contacting the resin in counter-current flow with a dilute aqueous solution of a soluble salt comprising a polyvalent anion, e.g., sodium sulfate. After the resin has been converted to the sulfate form with commensurate removal of thiocyanate anions, the resin is contacted with aqueous alkali, e.g., sodium hydroxide to remove the sulfate and is then flushed with water to complete the regeneration.

The second stage resin is regenerated in a counter-flow by contacting the resin with aqueous alkali hydroxide to remove the formate anions followed by a water wash to complete the regeneration.

It is apparent that conjugate base anions of acids are present during various stages of the alkanolamine treating process and also during the procedures carried out to reclaim spent alkanolamine. It would be desirable to have a process for determining the concentration and type of anions present in the alkanolamine solution at various stages of the treating process to reduce costs associated with undercirculation, high corrositivity and poor treating of amine streams. It would also be desirable to monitor alkanolamine reclamation processes.

PRIOR ART

U.S. Pat. No. 2,628,191 to Sard discloses a method for determining when a cation exchanger has become exhausted which comprises measuring electrical conductivity of the effluent from the resin bed and comparing that measurement against the conductivity trace of a portion of effluent which is passed through a different quantity of exchange material, such as a small auxiliary ion exchanger for testing.

U.S. Pat. No. 3,246,759 to Matalon discloses means for measuring the conductivity of a solution downstream of a resin bed for controlling the regeneration of ion exchange bed.

U.S. Pat. No. 3,531,252 to Rivers discloses a method of analyzing conductive solutions wherein the ionic constituent concentration of a sample is determined by: taking a first conductivity reading thereof; adding a reagent such that a substantial excess beyond the point of neutralization will not affect the conductivity of the solution and capable of reacting with said substituent in an amount in excess of that necessary for reaction; taking a second conductivity measurement; comparing the conductivities against a conductivity trace of known concentration of said constituent reaction with known quantities of reagent.

U.S. Pat. No. 4,199,323 to Miller et al provides an example of differential conductivity detection combined with ion exchange derivitization.

U.S. Pat. No. 4,242,097 to Rich et al discloses a system wherein a conductivity cell and its associated readout are provided for effluent detection of a solution which has been passed through an ion exchange column.

U.S. Pat. No. 4,814,281 to Byers discloses a monitoring system wherein conductivities of a solution are taken before and after passing a solution through an ion exchange column, and the differential conductivity is used to calculate sulfate concentration in accordance with a known relationship between a conductivity differential and sulfate concentration of a fluid sample.

U.S. Pat. No. 4,880,513 to Davis et al discloses a conductivity monitor which detects concentration of a circulation salt, while a second monitor detects concentrations of acid/base solutions which are utilized to regenerate exhausted ion exchange resins.

THE INVENTION

The invention relates to a process for monitoring the anion concentration in an alkanolamine solution. In one aspect of the invention, an alkanolamine solution containing anions is introduced to a contacting zone. A stirrer and a conductance probe connected through a meter to a recorder which provides a conductance trace with time, are also provided. In the contacting zone, the alkanolamine solution is stirred, preferably at a constant rate and a solid strong base anion exchange resin in the $OH^-$ form in an amount in excess of that required to exchange all of the anions from the alkanolamine solution is introduced to the contacting zone, and the conductivity of the alkanolamine solution on the conductance trace is monitored over time to determine qualitatively the composition and concentration of anions in the alkanolamine solution during exchange of the anions from the alkanolamine solution to the exchange resin.

In another aspect of the invention, the conductance of the alkanolamine solution in the contacting zone is monitored until steady state is reached at which point the total anion content of the alkanolamine solution is determined from the recorder conductance trace.

In further aspects of the invention, sodium ions are also present in the alkanolamine solution and the concentration of these ions is also determined.

BRIEF DESCRIPTION OF THE DRAWINGS

FIG. 5, 6 and 7 are other conductance traces of an alkanolamine solution containing anions and (in 6 and 7) sodium cations to which a strong base anion exchange resin has been added.

DETAILED DESCRIPTION OF THE INVENTION

Each anion found in the amine solutions has a conductance which generally differs from the conductance of the other anions. The same holds true for cations, such as $Na^+$. Equivalent conductances in aqueous solutions at 25° C. for the anions and cations of interest are set forth in the table.

TABLE

| ION | EQUIVALENT CONDUCTANCE MILLI SIEMENS |
|---|---|
| $Na^+$ | 50 |
| $Cl^-$ | 76 |
| $SO_4^-$ | 80 |
| $HCOO^-$ | 54 |
| $CH_3COO^-$ | 41 |
| $SCN^-$ | 65 |
| $MDEAH^+$ | 30 |
| $OH^-$ | 199 |

The process of the invention may be used to monitor any aqueous alkanolamine solution which contains anions. Such anions may be present in the form of alkali metal salts and/or alkanolamine salts. As previously pointed out, such alkanolamine solutions may result from processes in which hydrocarbon gases are contacted with an aqueous alkanolamine solution to absorb from said gases such impurities as $H_2S$ and $CO_2$. The resulting solutions which contain alkanolamine salts of $H_2S$ and $CO_2$ also may contain salts of various inorganic and organic anions which are present in the hydrocarbon gases or are formed in the solution by oxidation resulting from oxygen entering the alkanolamine treating system such as those listed in the Table. The alkanolamine salts may be converted to alkali metal salts by introducing an alkali metal hydroxide to the alkanolamine solution. Any alkali metal hydroxide may be used for this purpose such as potassium hydroxide or lithium hydroxide; however, for economic reasons, sodium hydroxide is preferred.

The process of the invention may be used to monitor alkanolamine solutions in order to determine the concentration and type of acid anions present in the solutions at various stages of the treating process. The process may be used to reduce problems associated with potential under-circulation of alkanolamine high corrositivity and poor treating of the amine streams. It may also be used to monitor amine reclamation (regeneration) processes.

Figure 1:
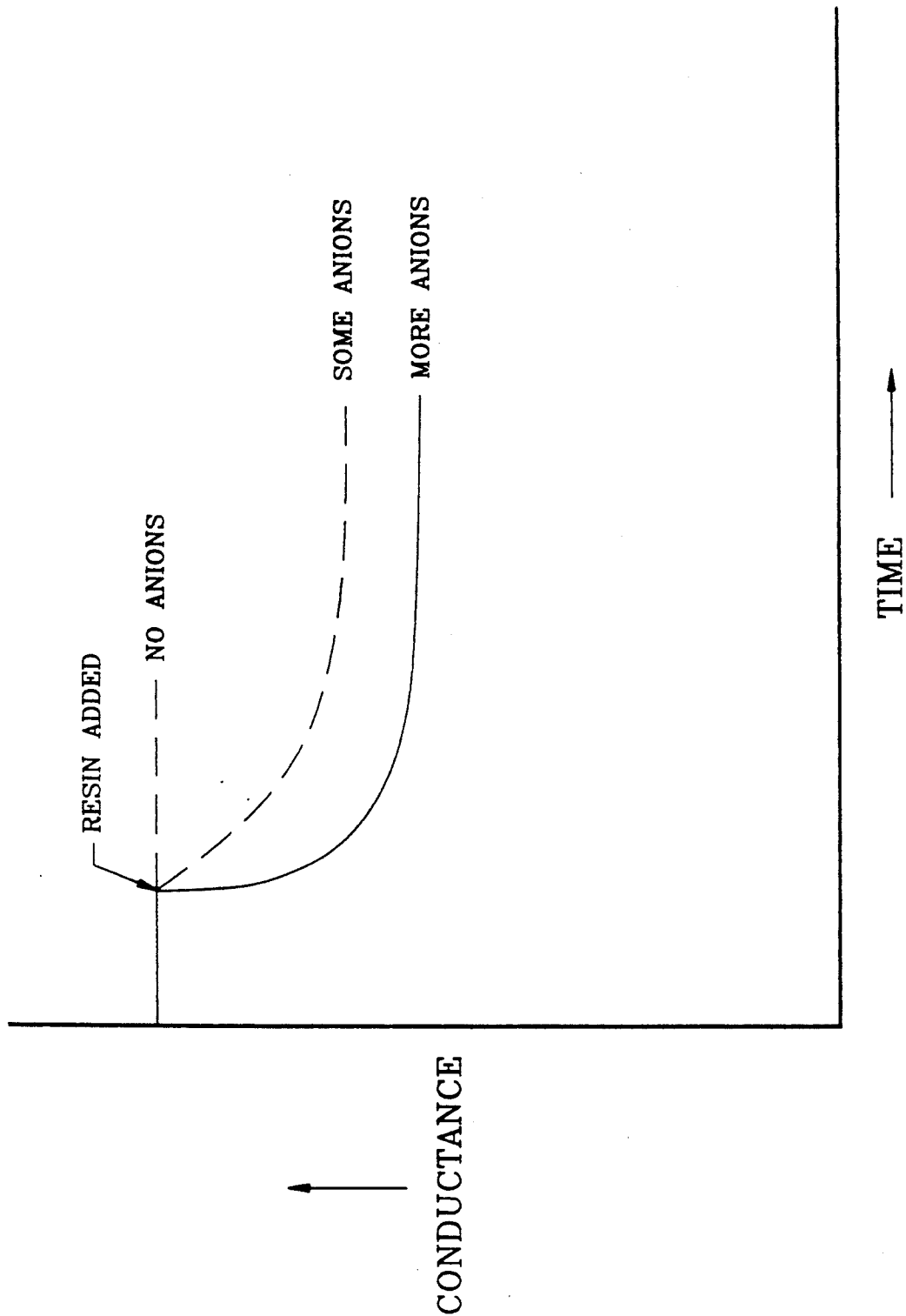
FIG. 1 is a conductance trace (conductance plotted versus time) of an alkanolamine solution containing various amounts of anions to which a basic anion exchange resin has been added.

In carrying out the process of the invention, a beaker or other suitable container is provided with a stirrer and a conductance probe which is connected through a meter to a recorder which provides a conductance trace with time. An alkanolamine solution containing anions such as those previously described is introduced to the container and stirring of the solution is commenced at a constant rate. The amount of anions present in the alkanolamine solution will vary depending on the type of process in which alkanolamine has been used. Usually the total anions in the alkanolamine solution will not exceed about 3 milliequivalents/milliliter of alkanolamine solution. A solid strong base anion exchange resin in the OH⁻ form is added to the container in an in excess of that required to exchange all of the anions from the alkanolamine solution. If desired stirring can commence with the addition of the exchange resin, although some prior stirring is preferred. Deionized water may be added to the solution prior to or during stirring to reduce the viscosity of the solution and improve the contact of the anions with the ion exchange resin. The conductance of the solution which is at a certain level before the basic anion exchange resin is added decreases with time as the acidic anions are exchanged from the alkanolamine solution. The process which takes place is illustrated in FIG. 1 in which the conductance of an alkanolamine solution containing anions is plotted with time as the anions are exchanged with a strong base anion exchange resin. It is noted from the figure that the conductance of the alkanolamine solution remains constant with time until resin is added to the solution. If there were no anions in the solution, the conductance would continue level as shown by the dashed line in the figure. However, anions are present and as they are exchanged from the alkanolamine solution the conductance gradually decreases with time and eventually levels out when all of the anions have been exchanged. Two curves are shown in FIG. 1. The upper curve represents conductance values obtained with some acidic anions being present in the alkanolamine solution. The lower solid curve illustrates the resulting conductance with a larger amount of anions in the alkanolamine solution.

The conductance of the alkanolamine solution illustrated in FIG. 1 decreases as a result of the following reaction:

$$RNH^+ + A^- + Res\text{-}OH \rightarrow RN + Res\text{-}A + H_2O$$

where
RN = alkanolamine
RNH⁺ = protonated amine
A⁻ = anion
Res-OH = anion exchange resin in OH⁻ form
Res-A = anion exchange resin with A⁻ in place of OH⁻

The conductance decreases because charged species are converted to uncharged species.

There are a number of factors which affect the shape of the conductance curves obtained in the process of the invention. These include the anion exchange rate with the resin which may vary from ion to ion and with resin type and particle size of the resin, the mixing rate employed, the equivalent conductance of respective anions, the concentration of respective ions in the test solution, the concentration of resin in the test solution, and the concentration of amine in the test solution. Variables such as resin type and particle size, mixing rate, concentration of resin and concentration of amine may be controlled at desired levels. With appropriate control of these variables it is possible to determine at least qualitatively the concentration of various anions in alkanolamine solutions by comparing the conductance curves obtained for such solutions with standardized curves in which the concentration of various ions in the alkanolamine solutions is known. It is also possible through the use of such standardized curves to determine the total anion content of an alkanolamine solution.

Figure 2:
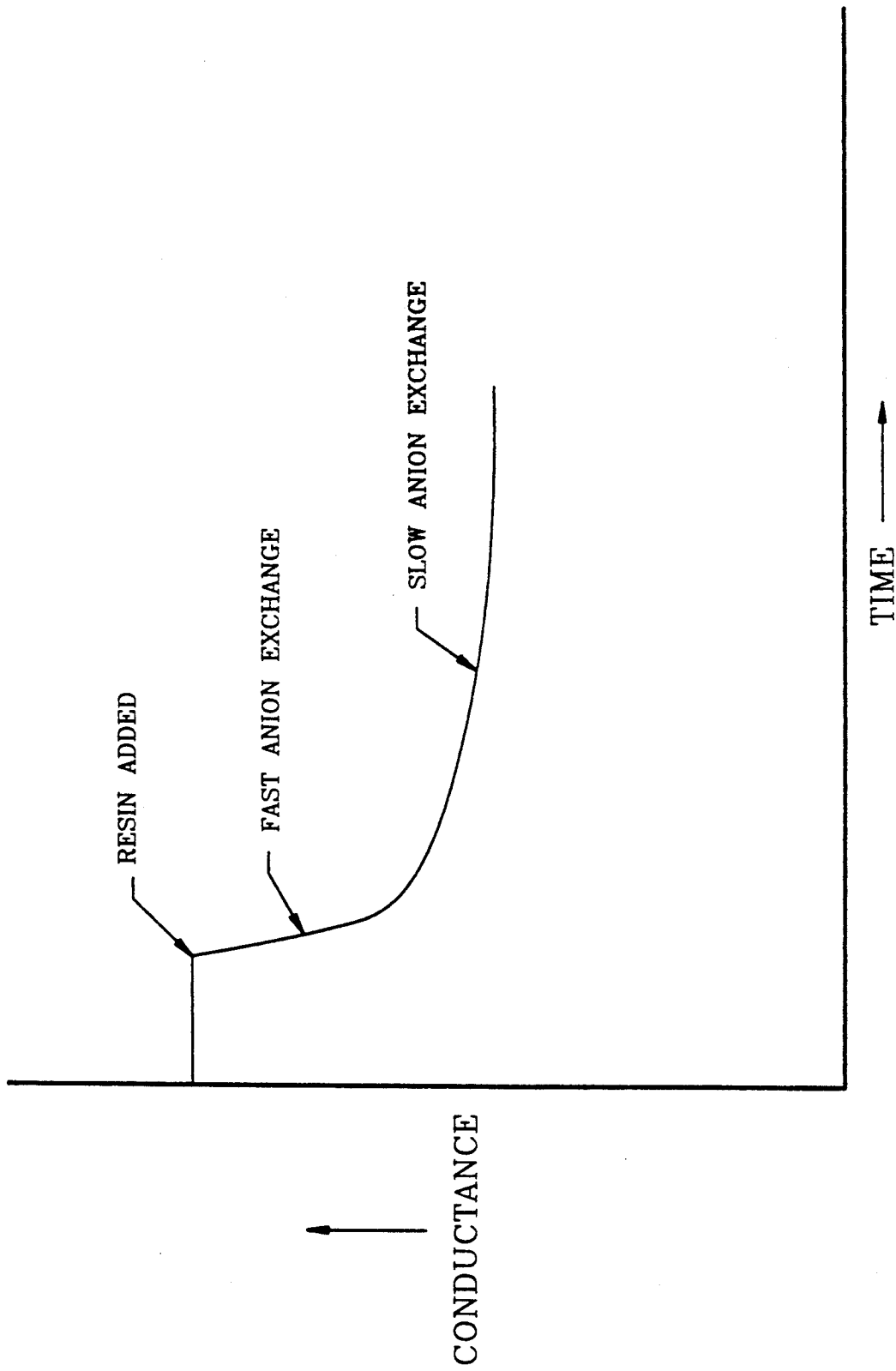
FIG. 2 is a conductance trace of an alkanolamine solution containing anions to which a strong base anion exchange resin has been added. A portion of the anions exchange rapidly with the resin while other anions exchange slowly.

The rate of change of a conductance curve may be used to distinguish the types of anions which are present in an alkanolamine solution. For example, FIG. 2 shows a conductance trace of an alkanolamine solution containing some anions which exchange with the resin at a relatively fast rate and other anions which exchange with the resin at a slower rate. As shown in the figure, the slope of the conductivity curve for the faster exchange anions is much steeper than the slope for the anions which exchange at a slower rate. FIG. 2 is a good example of a conductance trace in which the rate of change of the conductance curve may be used to characterize the anions which are present in an alkanolamine solution.

Figure 3:
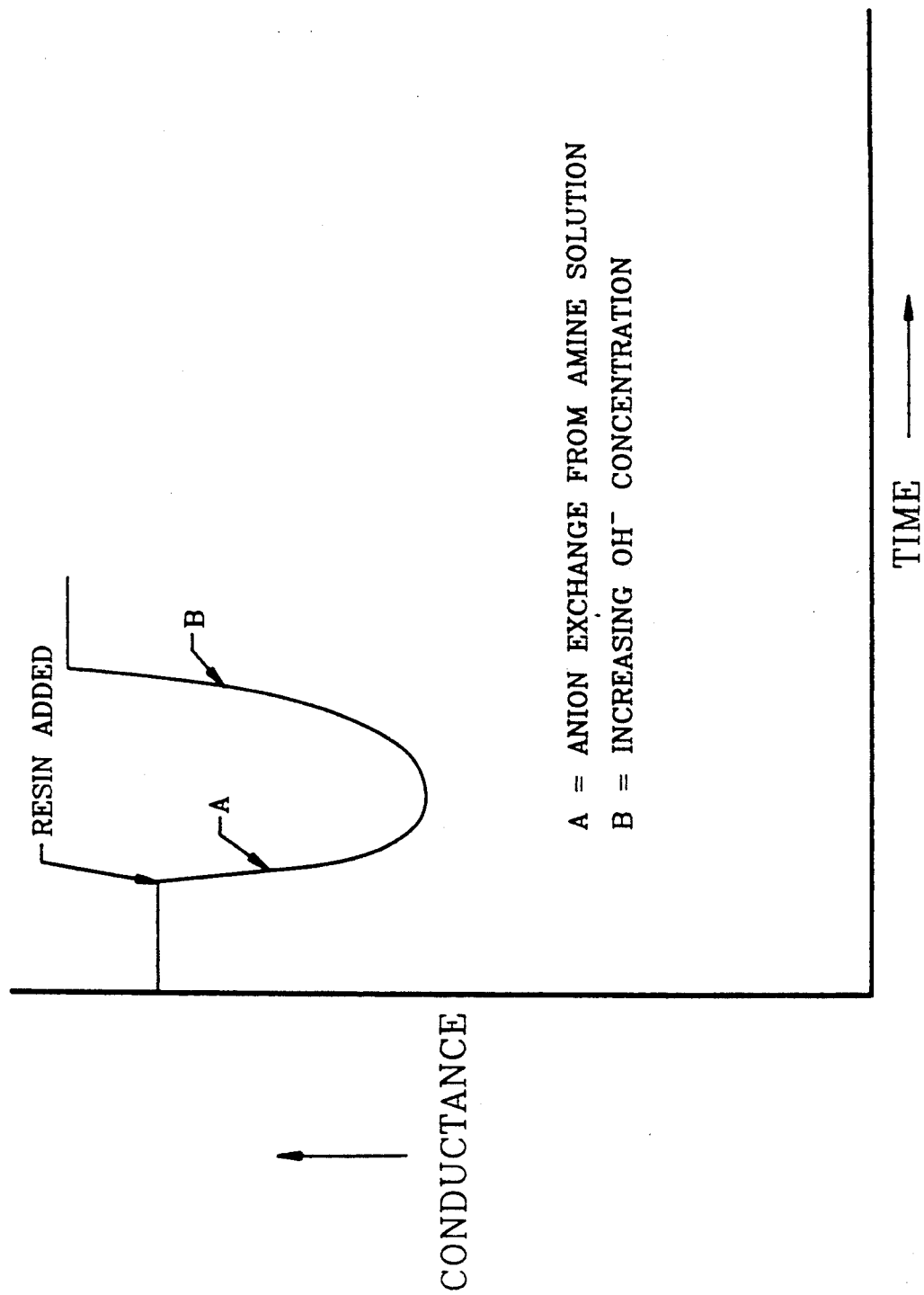
FIG. 3 is a conductance trace of an alkanolamine solution containing anions and sodium cations to which a strong base anion exchange resin has been added.

As pointed out previously, the alkanolamine salts of the anions may be converted to alkanolamine salts of alkali metals by introducing an alkali metal hydroxide such as sodium hydroxide to the alkanolamine solution. When this procedure is used, the alkanolamine solution will then contain sodium cations, as well as anions. The conductance trace obtained with an alkanolamine solution containing sodium cations is entirely different in shape as is illustrated by FIG. 3. The portion of the conductance curve designated "A" results from the following reaction:

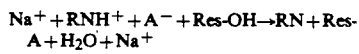

$$Na^+ + RNH^+ + A^- + Res\text{-}OH \rightarrow RN + Res\text{-}A + H_2O + Na^+$$

Here again the conductance of the alkanolamine solution decreases because charged species are converted to uncharged species.

If anions remain in the alkanolamine solution after all of the protonated amine is neutralized as shown in the above reaction, the direction of the conductance curve changes and begins to increase as shown in portion "B" of the curve in FIG. 3. This increase in the conductance curve results from the following reaction:

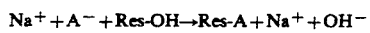

$$Na^+ + A^- + Res\text{-}OH \rightarrow Res\text{-}A + Na^+ + OH^-$$

The conductance of part "B" of the conductance curve increases because the equivalent conductance of OH⁻ is much greater than the other anions. The final conductance may exceed the initial conductance of the alkanolamine solution if enough OH⁻ is produced.

Conductance traces like the trace shown in FIG. 3 may be used to determine both the anion content and the sodium cation content of an alkanolamine solution.

Figure 4:
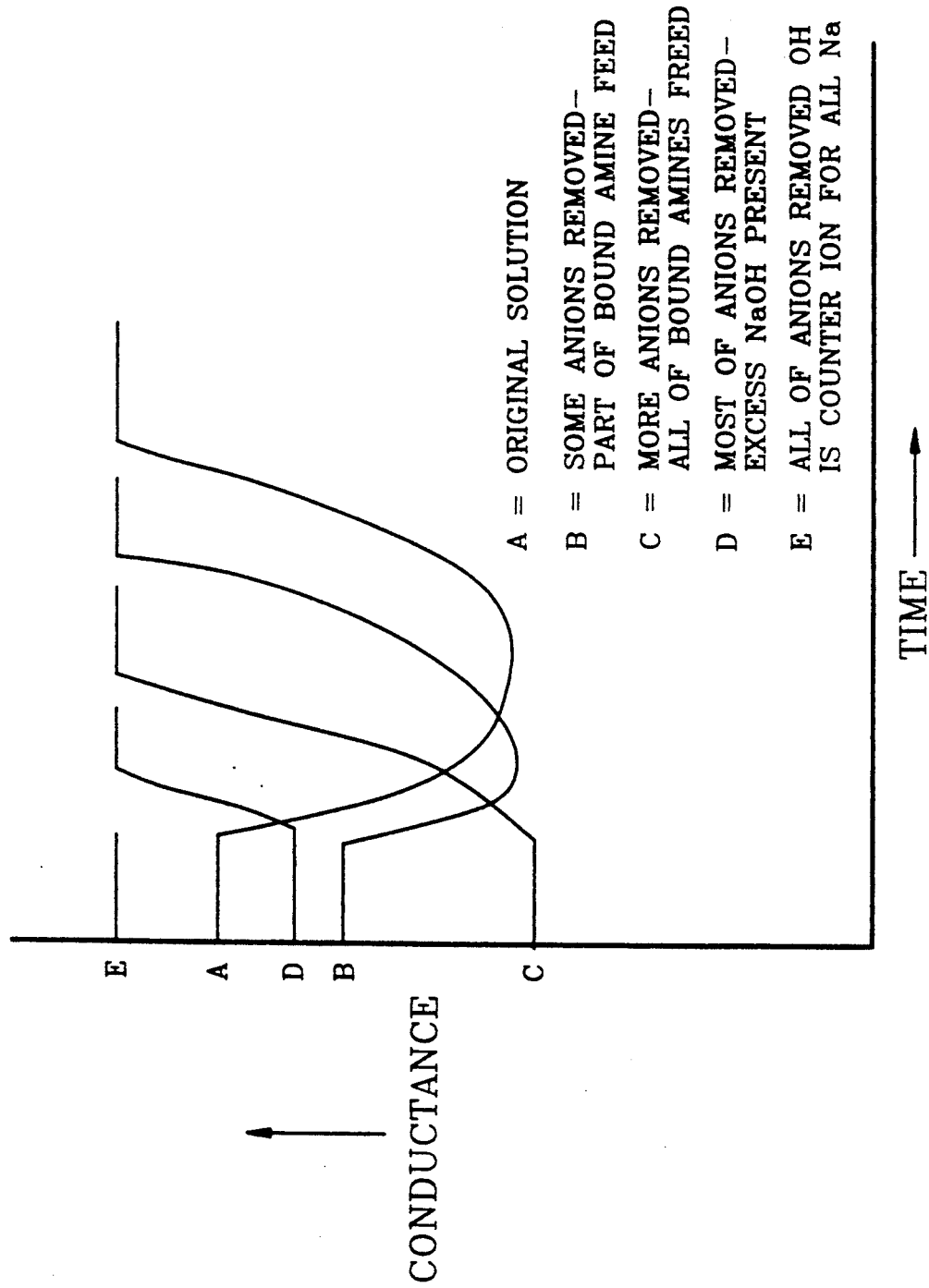
FIG. 4 is a series of conductance traces of alkanolamine solutions containing anions and sodium cations to which a strong base anion exchange resin has been added. The figure illustrates the conductance traces of samples of the alkanolamine solution taken at various stages of the anion removal during a reclamation process.

The use of the process of the invention to monitor the reclamation of alkanolamine solutions containing anions and sodium ions is illustrated in FIG. 4 where conductance traces are produced from samples taken at various stages during the reclamation process.

In this figure, line "A" represents the original solution, similar to the trace shown in FIG. 3. Trace "B" represents a stage of the reclamation process where some anions have been removed thus freeing part of the amine. In trace "C", a later stage of the process is reached in which more anions have been removed and all of the protonated amine has been freed. In trace "D" which is at a still later stage of the process, most of the anions have been removed. Trace "E" represents the completion of the process in which all of the anions have been removed and OH⁻ is the counter ion for all of the sodium ions.

The following examples are presented to illustrate the invention and not to limit it:

EXAMPLE 1

2.72 grams of methyldiethanolamine solution containing anions was diluted with water to 45 ml and placed in a 60 ml beaker. The MDEA solution contained 0.074 milliequivalents of formate ion per gram of solution, 0.005 milliequivalents of acetate ion per gram, and 0.039 milliequivalents of thiocyanate ion per gram of solution. The bound amine was 0.136 milliequivalents/gm of solution and the free amine was 2.90 milliequivalents/gm of solution. No sodium was present in the MDEA solution. A Teflon coated magnetic bar was placed in the beaker and the beaker was positioned on top of a magnetic stirrer operated by a variable speed motor. A YSI (Yellow Springs Instrument) dip type conductivity cell YSI No. 3417 was positioned in the beaker and connected to a YSI model 32 conductance meter. The conductance meter in turn was connected to a an Omniscribe TM chart recorder, Model D 5127-5 (Industrial Scientific, Inc.) so as to provide a conductance trace during the experiment.

Figure 5:
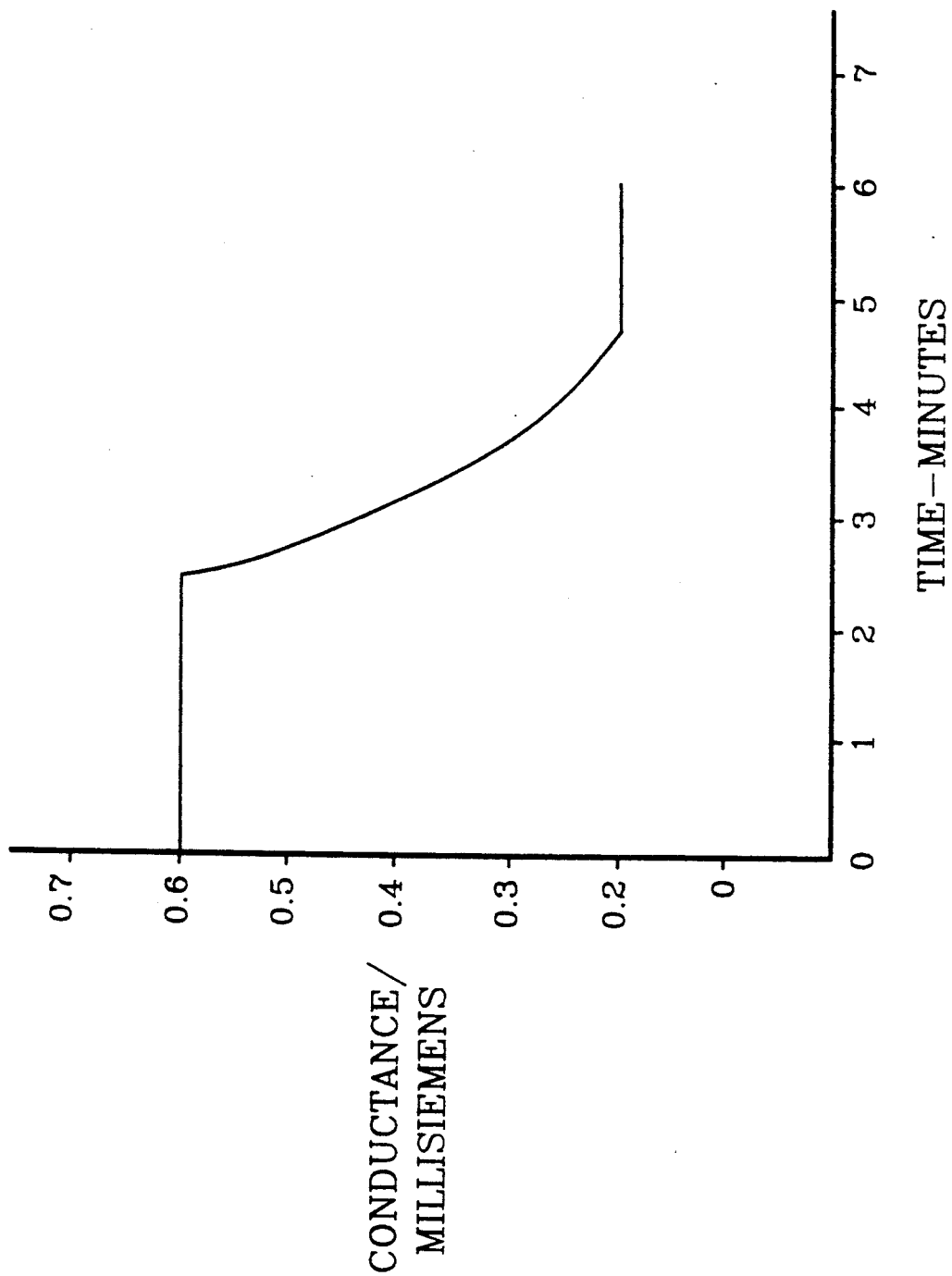

With the conductance meter and chart recorder operating, the contents of the beaker were stirred for two and one half minutes, after which 2.0 grams of resin was added to the MDEA solution. The resin used was Resin Tech SBG II, Type II which is a strong base anion exchange resin. The results of the tests are shown in FIG. 5. It is noted from the figure that the conductance of the MDEA solution remained constant at 0.60 milliSiemens for the 2½ minutes during which the water and the MDEA solution only were present in the beaker. With the addition of the resin at the end of 2½ minutes, the conductance of the MDEA solution immediately decreased in magnitude and at the expiration of five minutes had reached a magnitude slightly less than 0.2 milli Siemens. After this point in time the conductance of the solution remained constant indicating complete exchange of the anions present in the solution with the exchange resin.

EXAMPLE 2

The apparatus used in this example was the same as that used in Example 1. However, the amine solution was of different composition and quantity. The amine solution used in this test contained 0.78 milliequivalents of sodium per gram, 0.63 milliequivalents of acetate per gram of solution, 0.52 milliequivalents of formate per gram of solution, 0.27 milliequivalents of thiocyanate per gram of solution, 0.07 milliequivalents of chlorine per gram of solution, and 0.03 milliequivalents of sulfate per gram of solution. 0.42 grams of MDEA solution were used in the test. The total amine present was 4.0 milliequivalents per gram of solution and the bound amine was 0.66 milliequivalents per gram of solution.

Figure 6:
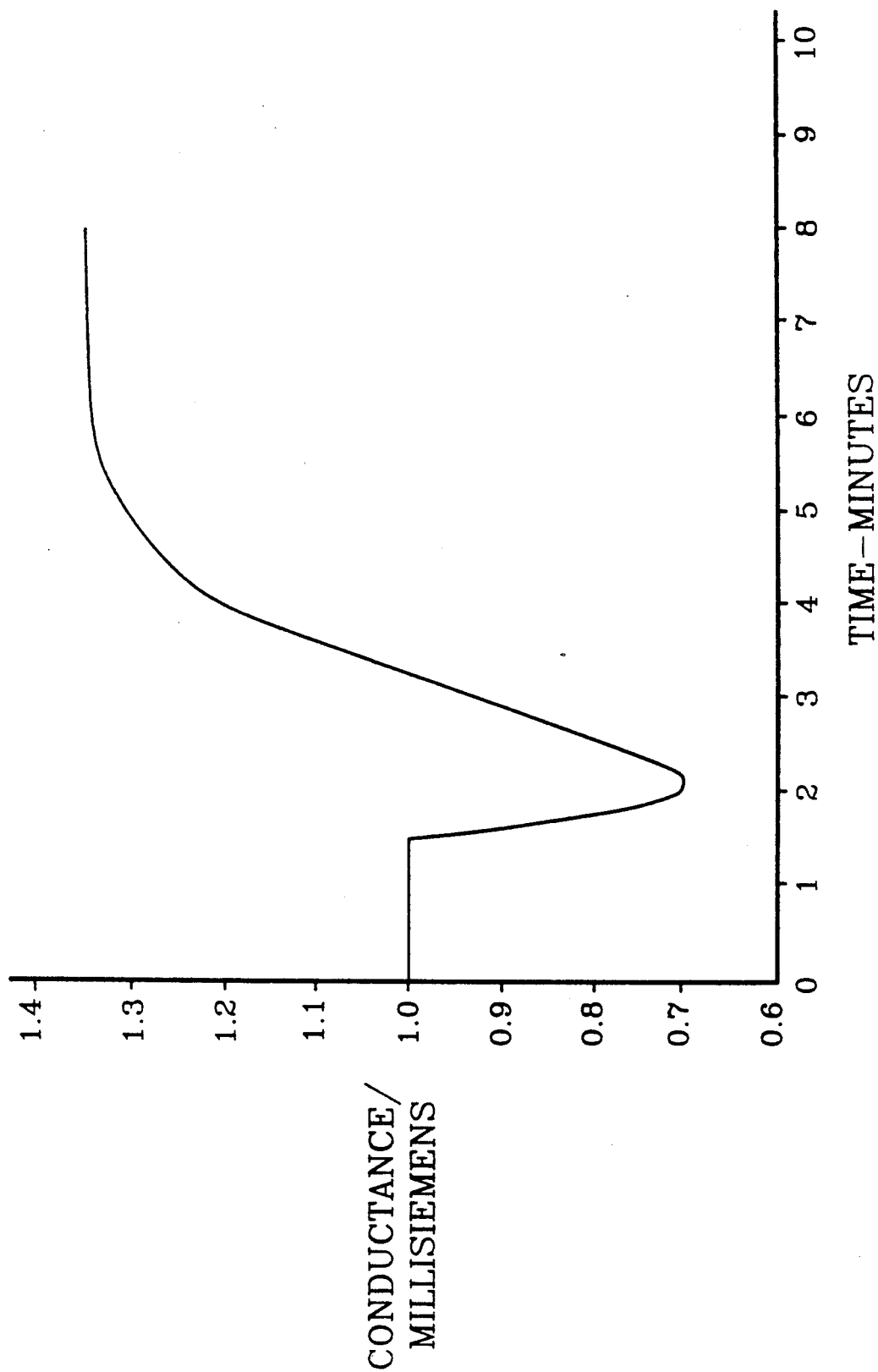

The results of the test are shown in FIG. 6. The MDEA solution initially had a conductance of 1.0 which remained constant during 1.5 minutes of stirring until the ion exchange resin in the amount of 2.0 grams was added to the solution. With the addition of the resin, the conductance of the solution dropped sharply reaching a minimum conductance of 0.7 in approximately 0.6 minutes. This drop reflects the exchange of the anions from the alkanolamine solution.

As stirring was continued, the conductance of the solution increased rapidly, reached a level of 1.34 milliSiemens by 5.5 minutes after addition of the ion exchange resin, and thereafter remained at this level. This sharp rise in conductance reflects the exchange of excess anions with resin in the solution and the increase in the solution of $OH^-$ ions which have an equivalent conductance much greater than any of the other anions. As a result, the conductance of the solution increased to a level substantially higher than the starting conductance.

EXAMPLE 3

A test was carried out under the same conditions as Example 2 except that 4.0 grams of resin were added to the beaker rather than 2.0 grams. The results of the test are shown in FIG. 7. A comparison of FIGS. 6 and 7 shows that the minimum conductance reaches 0.75 in 0.3 minutes in FIG. 7 as compared to 0.7 in 0.6 minutes in FIG. 6. The rate of change in conductance of the solution when the release of $OH^-$ ions begins is much greater in FIG. 7. The maximum conductance figure is reached in FIG. 7 in approximately three minutes, whereas the time required in FIG. 6 with the laser amount of ion exchange resin was almost six minutes. This may be explained by the fact that more sites were available for exchange with the anions with the increased amount of resin. The presence of more sites may also explain the higher final conductance of the solution obtained in this example.

The apparatus used for carrying out the process of the invention may be obtained from a large number of sources. For example, Fisher Scientific markets a number of magnetic stirrers, probes, conductance meters and chart recorders. Fisher also supplies this type of equipment under the names of other manufacturers. For example, Corning Probes and Meters, Barnsted Probes and Meters, Sargeant-Welch and Linear Chart Recorders. Two other supply houses, Thomas and Van Waters and Rogers also supply this type of equipment under their own names and under other brand names.

A variety of ion exchange resins may be used in the process of the invention. Strong base anion exchange resins are characterized as having fixed tertiary amine anion exchange sites which are positively charged at any pH. Weak base anion exchange resins have fixed primary or secondary amine anion exchange sites. The sites are positively charged depending on the pH of the solution. At higher pH the sites are neutral.

Type I resins are those which contain amine groups. Type II resins contain alkanolamine groups. Examples of strong base Type I anion exchange resins are styrene-divinylbenzene resins with quaternary ammonium groups attached to the polymer framework such as Resintech TM SBG-1 and Sybron TM ASB-I. Strong base Type II anion exchange resins include styrene-divinylbenzene resins with quaternary ammonium groups attached to the polymer framework, such as Resintech TM SBG-II and Sybron TM ASB-II.

Other resins which may be used include such materials as Mobay TM M500, a Type I strong base anion exchange resin, which is a polystyrene resin with quaternary ammonium groups attached to the polymer framework; Rohm and Haas Amberlyst TM A-26, a Type I strong base anion exchange resin, which is a styrene/divinylbenzene copolymer with quaternary ammonium groups attached to the polymer framework and Rohm and Haas Amberlite TM IRA-410, a Type II strong base amine-type anion exchange resin. Also included are DOW styrenedivinylbenzene strong base anion exchange resins having quaternary amines as their functional group. These materials are available are available under the DOWEX trademark.

While any of the above and other anion exchange resins may be used, the resins preferred for use are the strong base ion exchange resins.

While magnetic stirring has been described, other types of stirrers may be used in carrying out the process of the invention. While it is important to stir rapidly to provide good mixing, the stirring is normally limited to a speed such that no vortex forms in the alkanolamine solution.

While certain embodiments and details have been shown for the purpose of illustrating the present invention, it will be apparent to those skilled in the art that various changes and modifications may be made herein without departing from the spirit or scope of the invention.

I claim:

1. A process for directly monitoring the anion concentration in an alkanolamine solution which comprises:
   (a) introducing an alkanolamine solution containing anions to a contacting zone;
   (b) thereafter introducing to the contacting zone a solid anion exchange resin in the $OH^-$ form in an amount in excess of that required to exchange all of the anions from the alkanolamine solution;
   (c) stirring the contents of the contacting zone and measuring and recording the conductance of the alkanolamine solution during and after addition of the ion exchange resin;
   (d) monitoring the conductance of the alkanolamine solution until steady state is reached; and
   (e) determining the total anion content of the alkanolamine solution from the recorded conductance trace.

2. The process of claim 1 in which the anions are selected from the group consisting of hydrated acid gases and anions consisting of $SO_2$, COS, HCN, $S_2O_3^=$, $SO_4^=$, $SCN^-$, $HCO_2^-$, $CH_3CO_2^-$ and $CL^-$.

3. The process of claim 1 in which the alkanolamine is selected from the group consisting of ethanolamine, diethanolamine, methyldiethanolamine, diisopropanolamine and triethanol amine.

4. A process for directly monitoring the anion and sodium cation concentration in an alkanolamine solution which comprises:
   (a) introducing an alkanolamine solution containing anions and sodium cations to a contacting zone;
   (b) thereafter introducing to the contacting zone a solid anion exchange resin in the $OH^-$ form in an amount in excess of that required to exchange all of the anions from the alkanolamine solution;
   (c) stirring the contents of the contacting zone and measuring and recording the conductance of the alkanolamine solution during and after addition of the ion exchange resin;
   (d) monitoring the conductance of the alkanolamine solution until steady state is reached; and
   (e) determining the total anion content and the sodium cation content of the alkanolamine solution from the recorded conductance trace.

5. The process of claim 4 in which the anions are selected from the group consisting of hydrated acid gases and acidic anions consisting of $SO_2$, COS, HCN, $S_2O_3^=$, $SO_4^=$, $SCN^-$, $HCO_2^-$, $CH_3CO_2^-$ and $CL^-$, 6. The process of claim 5 in which the alkanolamine is selected from the group consisting of ethanolamine, diethanolamine, methyldiethanolamine, diisopropanolamine and triethanol amine.

7. A process for directly monitoring the anion concentration in an alkanolamine solution which comprises:
   (a) introducing an alkanolamine solution containing anions to a contacting zone;
   (b) providing in the contacting zone a stirrer and a conductance probe connected through a meter to a recorder which provides a conductance trace with time;
   (c) stirring the alkanolamine solution;
   (d) introducing to the contacting zone a solid anion exchange resin in the $OH^-$ form in an amount in excess of that required to exchange all of the anions from the alkanolamine solution;
   (e) monitoring the conductance of the alkanolamine solution until steady state is reached; and
   (f) determining the total anion content of the alkanolamine solution from the recorder conductance trace.

8. The process of claim 7 in which step (f) is accomplished by comparing the recorder conductance trace to standard recorder conductance traces on known compositions and concentrations of anions in alkanolamine solutions.

9. The process of claim 7 in which the anions are selected from the group consisting of hydrated acid gases and anions consisting of $SO_2$, COS, HCN, $S_2O_3^=$, $SO_4^=$, $SCN^-$, $HCO_2^-$, $CH_3CO_2^-$ and $CL^-$.

10. The process of claim 7 in which the alkanolamine is selected from the group consisting of ethanolamine, diethanolamine, methyldiethanolamine, diisopropanolamine and triethanol amine.

11. A process for directly monitoring the anion and sodium cation concentration in an alkanolamine solution which comprises:
    (a) introducing an alkanolamine solution containing anions and sodium ions to a contacting zone;
    (b) providing in the contacting zone a stirrer and a conductance probe connected through a meter to a recorder which provides a conductance trace with time;
    (c) stirring the alkanolamine solution;
    (d) introducing to the contacting zone a solid anion exchange resin in the $OH^-$ form in an amount in excess of that required to exchange all of the anions from the alkanolamine solution;
    (e) monitoring the conductance of the alkanolamine solution until steady state is reached; and
    (f) determining the total anion content and the sodium cation content from the recorded conductance trace.

12. The process of claim 11 in which step (f) is accomplished by comparing the recorder conductance trace to standard recorder conductance traces of known compositions and concentrations of anions and sodium cations in alkanolamine solutions.

13. The process of claim 11 in which the anions are selected from the group consisting of hydrated acid gases and anions consisting of $SO_2$, COS, HCN, $S_2O_3^=$, $SO_4^=$, $SCN^-$, $HCO_2^-$, $CH_3CO_2^-$ and $CL^-$.

14. The process of claim 11 in which the alkanolamine is selected from the group consisting of ethanolamine, diethanolamine, methyldiethanolamine, diisopropanolamine and triethanol amine.

15. A process for characterizing the composition of an alkanolamine solution containing anions which comprises:

(a) introducing an alkanolamine solution containing anions to a contacting zone;

(b) providing in the contacting zone a stirrer and a conductance probe connected through a meter to a recorder which provides a conductance trace with time;

(c) stirring the alkanolamine solution;

(d) introducing to the contacting zone a solid anion exchange resin in the $OH^-$ form in an amount in excess of that required to exchange all of the anions from the alkanolamine solution;

(e) monitoring the conductance of the alkanolamine solution on the recorder conductance trace and determining qualitatively the composition and concentration of anions in the alkanolamine solution during the exchange of the anions from the alkanolamine solution to the exchange resin.

16. The process of claim 15 in which step (e) is accomplished by comparing the recorder conductance trace to standard recorder conductance traces on known compositions and concentrations of anions in alkanolamine solutions.

17. The process of claim 15 in which the anions are selected from the group consisting of hydrated acid gases and anions consisting of $SO_2$, COS, HCN, $S_2O_3^=$, $SO_4^=$, $SCN^-$, $HCO_2^-$, $CH_3CO_2^-$ and $CL^-$.

18. The process of claim 15 in which the alkanolamine is selected from the group consisting of ethanolamine, diethanolamine, methyldiethanolamine, diisopropanolamine and triethanol amine.

19. A process for directly monitoring the anion and sodium cation concentration in an alkanolamine solution which comprises:

(a) introducing an alkanolamine solution containing anions and sodium ions to a contacting zone;

(b) providing in the contacting zone a stirrer and a conductance probe connected through a meter to a recorder which provides a conductance trace with time;

(c) stirring the alkanolamine solution;

(d) introducing to the contacting zone a solid anion exchange resin in the $OH^-$ form in an amount in excess of that required to exchange all of the anions from the alkanolamine solution; and (e) monitoring the conductance of the alkanolamine solution on the recorder conductance trace and determining qualitatively the composition and concentration of anions and sodium cations in the alkanolamine solution during the exchange of the anions from the alkanolamine solution to the exchange resin.

20. The process of claim 19 in which step (e) is accomplished by comparing the recorder conductance trace to standard recorder conductance traces for known compositions and concentrations of anions and sodium cations in alkanolamine solutions.

21. The process of claim 19 in which the anions are selected from the group consisting of hydrated acid gases and anions consisting of $SO_2$, COS, HCN, $S_2O_3^=$, $SO_4^=$, $SCN^-$, $HCO_2^-$, $CH_3CO_2^-$ and $CL^-$.

22. The process of claim 19 in which the alkanolamine is selected from the group consisting of ethanolamine, diethanolamine, methyldiethanolamine, diisopropanolamine and triethanol amine.

* * * * *

UNITED STATES PATENT AND TRADEMARK OFFICE
CERTIFICATE OF CORRECTION

PATENT NO.   :   5,208,164
DATED        :   May 4, 1993
INVENTOR(S)  :   Arthur L. Cummings It is certified that error appears in the above-identified patent and that said Letters Patent is hereby corrected as shown below:

Column 8, line 21, "laser" should be --lesser--.

Signed and Sealed this

Eleventh Day of January, 1994

Attest:

BRUCE LEHMAN

*Attesting Officer*    *Commissioner of Patents and Trademarks*